(12) United States Patent
Holmqvist

(10) Patent No.: US 9,125,986 B2
(45) Date of Patent: Sep. 8, 2015

(54) MEDICAMENT DELIVERY DEVICE

(75) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 1122 days.

(21) Appl. No.: 13/139,296

(22) PCT Filed: Dec. 8, 2009

(86) PCT No.: PCT/EP2009/066575
§ 371 (c)(1),
(2), (4) Date: Aug. 12, 2011

(87) PCT Pub. No.: WO2010/066706
PCT Pub. Date: Jun. 17, 2010

(65) Prior Publication Data
US 2012/0165753 A1    Jun. 28, 2012

Related U.S. Application Data

(60) Provisional application No. 61/122,371, filed on Dec. 13, 2008.

(30) Foreign Application Priority Data

Dec. 12, 2008 (SE) ...................................... 0850131

(51) Int. Cl.
*A61M 5/315* (2006.01)
*A61M 5/20* (2006.01)
*A61M 5/24* (2006.01)

(52) U.S. Cl.
CPC .............. *A61M 5/20* (2013.01); *A61M 5/31501* (2013.01); *A61M 5/31581* (2013.01); *A61M 5/24* (2013.01); *A61M 2005/2407* (2013.01); *A61M 2005/2488* (2013.01); *A61M 2005/2492* (2013.01)

(58) Field of Classification Search
CPC ............. A61M 2005/2407; A61M 2005/2488; A61M 5/31578; A61M 5/31581; A61M 5/31586; A61M 5/31501
USPC ......... 604/181, 207, 208, 211, 218, 224, 228, 604/220
See application file for complete search history.

(56) References Cited

U.S. PATENT DOCUMENTS 2,725,877 A * 12/1955 Reiter et al. ................... 604/135
6,648,850 B2 * 11/2003 Landau ........................... 604/70

FOREIGN PATENT DOCUMENTS

GB           2443390          *    5/2008

* cited by examiner

*Primary Examiner* — Matthew F DeSanto
(74) *Attorney, Agent, or Firm* — Piedmont Intellectual Property

(57) ABSTRACT

The present invention relates to a medicament delivery device (10) comprising a housing (12, 14); a medicament container (22) arranged inside the housing; a medicament delivery drive unit comprising a plunger rod (28) acting on said medicament container (22) and a power force (26) capable of driving said plunger rod (28) for delivering a dose of medicament. The invention is characterised in a delivery controller (30) comprising a manually operable release mechanism (30, 36) for releasing said plunger rod (28) and said power source (26) for delivering a dose of medicament and a manually operable control speed mechanism (30, 38) capable of controlling the speed of the released plunger rod and thereby the medicament delivery speed.

6 Claims, 4 Drawing Sheets

MEDICAMENT DELIVERY DEVICE

TECHNICAL AREA

The present invention relates to a medicament delivery device and in particular a delivery device with which the operator may control the delivery sequence.

TECHNICAL BACKGROUND

There are numerous devices for delivering medicament on the market and also patented where the medicament is arranged in a container, such as a syringe, cartridge and the like, and wherein the medicament is exposed to pressure when it is to be delivered. A very common design with for example injection devices is a generally tubular compartment having a stopper in one end of the compartment and a needle unit attached to the opposite end of the compartment.

In order to deliver a quantity of medicament, the stopper is exposed to pressure, i.e. pushed into the compartment by a pusher or plunger rod, which in many cases is performed by pressure means such as springs, which is common in automatic or semi-automatic injectors, whereby a delivery sequence is performed.

Usually the delivery sequence is triggered by a user manually pressing an activation button or a needle shield, which releases the spring acting on the plunger rod. The delivery sequence may also be triggered by the termination of a previous penetration sequence. In both instances, once the delivery sequence has been triggered, it continues until the dose is delivered, either when the medicament container is emptied or the delivery mechanism has reached a preset dose stop.

However, there may be instances when it is desirable for the user to take control over the delivery sequence. For example with injection of medicament into the tissue of the patient, it may for instance be that the injection hurts when the medicament expands into the tissue and the patient wants to take a pause without removing the injector or just wants to reduce the injection speed in order to the medicament to be absorbed by the tissue during the injection.

Some delivery devices are provided with electrically driven delivery mechanisms. For example the U.S. Pat. No. 6,474,219 discloses an injector arranged with a plunger rod acting on a stopper of a medicament container for expelling a dose of medicament through an injection needle. The plunger rod, in this case a helical compression spring that is driven forward by a piston drive comprising a nut element acting on the plunger rod, and an electrical motor driving the nut element. If the activation of the motor is controlled by the user, it is possible to stop the injection temporarily.

However, even if the above mentioned injector provides the possibility of temporarily stopping and starting the injection sequence, it is well known in art that there is a clear drawback to have medical devices depend on electric power in order for their function, and in particular to rely on electric power for delivery of the medicament. If for example the battery of the device would be depleted, it is impossible for the patient to receive a dose, which may be fatal to the patient.

A further drawback is that medicament devices operated by electrical components tend to be more expensive than purely mechanical devices. This is definitely true if the device is to be arranged with some sort of speed control means for the electrical motor in order for the user to be able to slow down, but not stop, the injection.

Other attempts have been made to solve this problem. Such solutions are shown in documents GB 2 443 390 and GB 2 071 499.

However, there is room for improvements regarding the size, the design and specially the ergonomics when manipulating the device.

There are thus a number of aspects that may be addressed with the present invention.

BRIEF DESCRIPTION OF THE INVENTION

The aim of the present invention is to provide a user-controlled delivery sequence of a delivery device.

This aim is obtained according to the present invention by the features of the independent patent claim.

Preferable embodiments of the present invention form the subject of the dependent patent claims.

According to a major aspect of the invention, it is characterised by a medicament delivery device comprising a generally elongated tubular housing comprising a front part and a rear part; a medicament container disposed within the front part, wherein the container has a front opening with or for a delivery member for delivering the medicament therethrough; a medicament delivery drive unit comprising a power source and a plunger rod, arranged to be moved between a cocked position and a released position within said medicament container with a determined speed; a manually operable delivery controller arranged to be moved between a locked position in which a release mechanism of said manually operable delivery controller holds said medicament delivery drive unit in its cocked position, and a releasing position in which said release mechanism releases the medicament delivery drive unit; wherein said manually operable delivery controller is further arranged to move between the releasing position and a controlling position in which a control speed mechanism of said manually operable delivery controller interacts with said medicament delivery drive unit for controlling the speed of the medicament delivery drive unit and thereby the medicament delivery speed, wherein the manually operable delivery controller comprises a scroll wheel segment protruding somewhat through an opening on the side of the rear part, and wherein said scroll wheel segment is arranged turnable around an axis.

According to a further aspect of the invention, the release mechanism is a ledge of the scroll wheel segment interacting with the front end of the plunger rod, such that when the front end of the plunger rod rests onto the ledge, the medicament delivery drive unit in is held in its cocked position; and when the scroll wheel segment is moved from the locked position to the releasing position, the ledge is disengaged from the front end of the plunger rod and the derive means are moved from the cocked position to the released position.

According to another aspect of the invention, the control speed mechanism is a contact surface of the scroll wheel segment interacting with a side surface of the plunger rod, such that when the scroll wheel segment is moved from the releasing position to the control position, the contact surface makes contact with the side surface of the plunger rod for controlling the speed of the medicament delivery drive unit and thereby the medicament delivery speed.

According to another aspect of the invention, the contact surface is arranged with friction enhancing members.

According to yet another aspect of the invention, the scroll wheel segment comprises a manually operating surface arranged with friction enhancing members.

According to yet a further aspect of the invention, the delivery member is a needle or a nozzle.

There are a number of advantages with the present invention. Because the delivery device is arranged with a manually operable delivery controller comprising a delivery release mechanism and a control speed mechanism the user can easily control the start of delivery as well as the delivery speed from maximum speed delivered by the power source to a complete stop for pausing the delivery sequence. This is of great benefit if for example the user wishes to temporarily stop the delivery or reduce the speed of delivery, such as could be the case during e.g. injection where the injected medicament causes pain, or during e.g. inhalation of medicament when the patient feel that he/she has not full control of the timing between inhalation and medicament delivery after releasing the delivery sequence.

Further, because the delivery controller is manually operated, it is always possible to obtain a dose of medicament even though the delivery controller is not used after activation of delivery. This is not the case when the delivery controller is electrically driven and the batteries or the like power source are depleted. In that case the delivery device does not function at all and the patient is unable to obtain a dose of medicament, which could be fatal.

The delivery controller comprises a turnable/scroll wheel segment. This design provides an intuitive scroll-like operation with for example the users thumb giving a better ergonomics of manipulation. It further becomes intuitive how the device is to be held during e.g. penetration and injection. The device is thus very easy to handle both regarding release of the plunger rod and the subsequent control of the speed of the plunger rod during medicament delivery.

In order to further facilitate the use and control of the delivery controller, either one or both of the speed control contact surface and the manually operating surface are arranged with friction enhancing members, such as protrusions, grooves, ridges, materials with high friction, such as rubber and the like, whereby the handling and control of the delivery of medicament is facilitated.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which FIG. 1 discloses a side-view of a first embodiment of the present invention.

DETAILED DESCRIPTION OF THE INVENTION

The embodiments shown in the FIGS. 1-4 refer to a medicament injection device.

Figure 1:
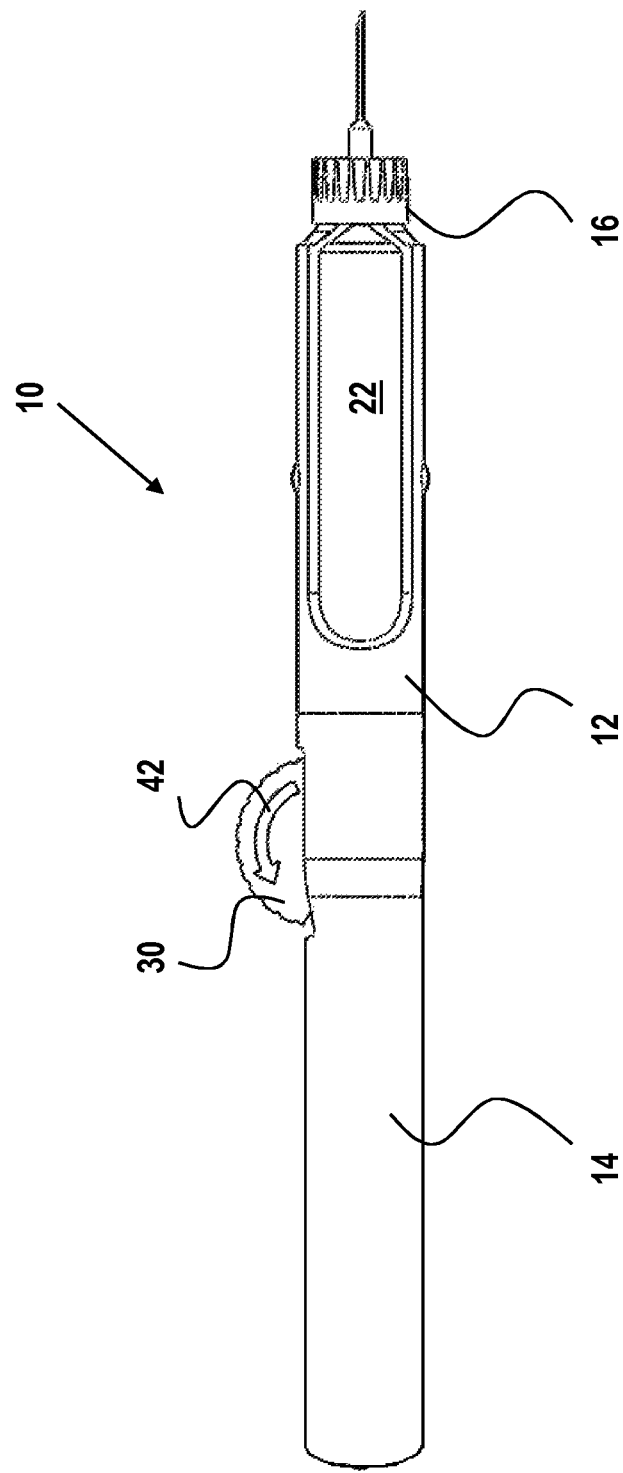
Figure 2:
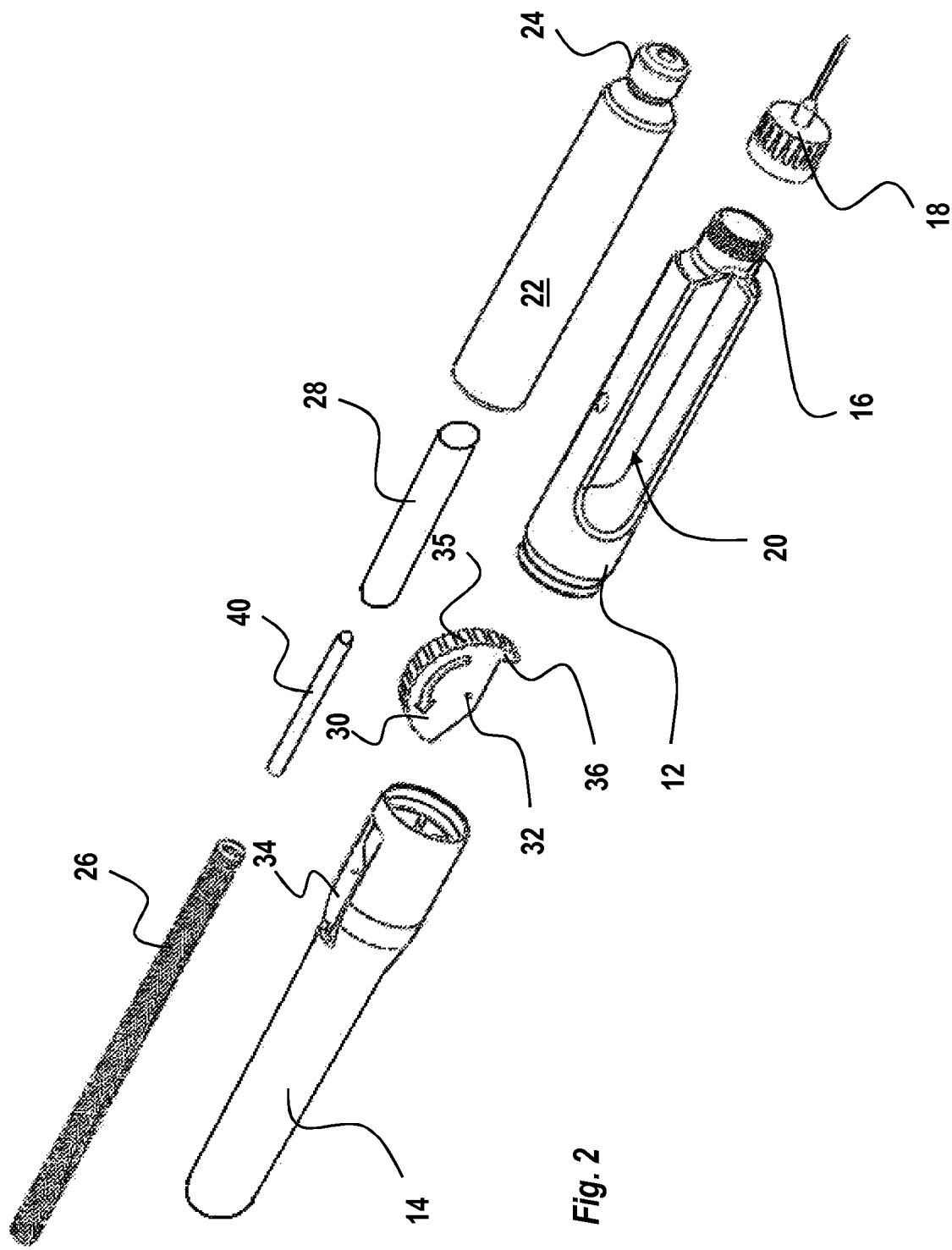
FIG. 2 is an exploded view of the injection device of FIG. 1, FIGS. 3-4 are cross-sectional views of the embodiment of FIG. 1 in different functional positions.

FIGS. 1 to 2 show a preferred embodiment of the present invention.

FIG. 1 shows an example of a medicament delivery device 10 comprising a generally elongated tubular housing consisting of two parts, a front part 12 and a rear part 14 that can be connected to each other in a suitable manner, for example releasibly, by threads, bayonet fittings, snap-in connectors or the like, or fixedly by deep grooves, by gluing, welding or the like depending on the application and intended use.

A medicament container 22 is disposed within the front part. The medicament container has a front opening with or for a delivery member for delivering the medicament therethrough and at least one movable stopper 25. The front part 12 comprises a neck 16 onto which a delivery member such as e.g. a needle 18 may be attached, with e.g. treads, bayonet fittings or the like, when the container used is a cartridge. The front part 12 of the housing is further arranged with cut-outs 20 through which the medicament container 22 is visible, FIG. 3.

The rear part 14 of the device is arranged with a medicament delivery drive unit comprising a power source 26 and a plunger rod 28, arranged to be moved between a cocked position and a released position within said medicament container with a determined speed for delivering the medicament and wherein the power source is a spirally wound compression spring 26. A manually operable delivery controller 30 is arranged to be moved between a locked position in which a release mechanism of said manually operable delivery controller holds said medicament delivery drive unit in its cocked position, and a releasing position in which said release mechanism releases the medicament delivery drive unit. Further, the compression spring is positioned within the plunger rod between a fixed rear wall of the rear housing and the inner surface of the front end of the plunger rod 28. When the medicament delivery drive unit is in the cocked position, the spring 26 is pre-tensioned and held in the pre-tensioned position together with the plunger rod by the manually operable delivery controller 30.

The manually operable delivery controller 30 is further arranged to move between the releasing position and a controlling position in which a control speed mechanism of said manually operable delivery controller interacts with said medicament delivery drive unit for controlling the speed of the medicament delivery drive unit and thereby the medicament delivery speed. The manually operable delivery controller comprises a scroll wheel segment 30 protruding somewhat through an opening 34 on the side of the rear part 14, and said scroll wheel segment is arranged turnable around an axis 32.

Figure 3:
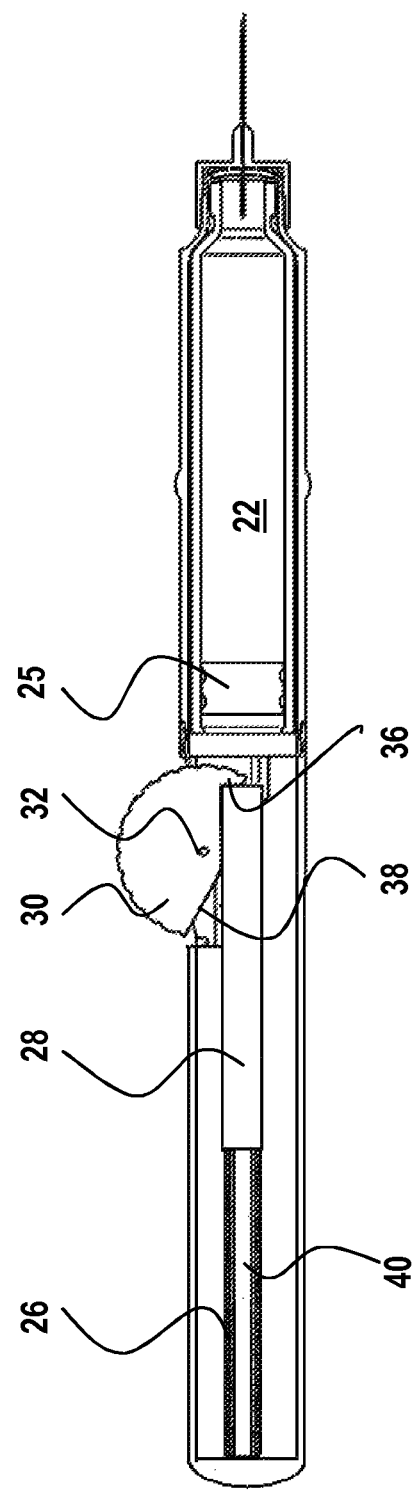
Figure 4:
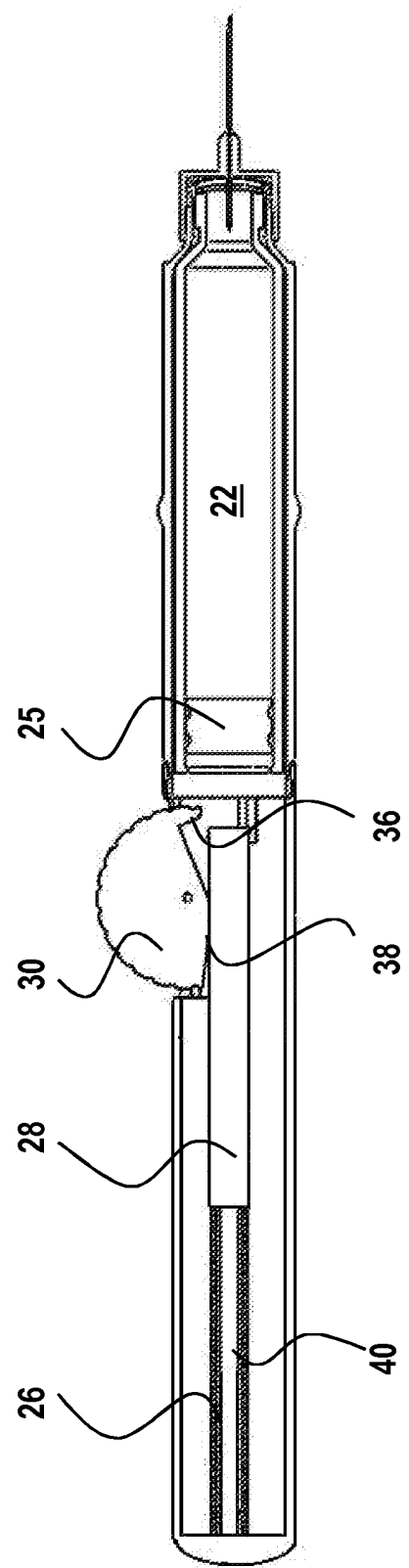

The release mechanism is a ledge 36 of the scroll wheel segment 30 interacting with the front end of the plunger rod, such that when the front end of the plunger rod 28 rests onto the ledge 36, FIG. 3, the medicament delivery drive unit in is held in its cocked position; and when the scroll wheel segment is moved from the locked position to the releasing position, the ledge 36 is disengaged from the front end of the plunger rod and the derive means are moved from the cocked position to the released position.

The control speed mechanism is a contact surface 38 of the scroll wheel segment 30 interacting with a side surface of the plunger rod 28, such that when the scroll wheel segment is moved from the releasing position to the control position, the contact surface 38 makes contact with the side surface of the plunger rod 28 for controlling the speed of the medicament delivery drive unit and thereby the medicament delivery speed.

The scroll wheel segment 30 also comprises a manually operating surface 35 arranged with friction enhancing members such as protrusions, grooves, ribs or the like, such that a user may operate the wheel with for example a thumb. In order to prevent buckling of the spring 26, a guide rod 40 is positioned inside said spring.

The device is intended to function as follows. The device could either be delivered completely assembled with the medicament container inside the housing, whereby the user merely has to attach a delivery member e.g. a needle 18 before use, or the device may be delivered without the medicament container 22, either in two halves 12, 14 or temporarily assembled, whereby the user has to insert a medicament container into the front housing and assemble the two parts, or the device is completely assembled with the medicament container inside the housing, wherein the medicament container has already the delivery member includes and which delivery member protrudes somewhat out from the front part, whereby the user merely has to remove a delivery member cover before use.

When the medicament is to be delivered, the device is activated by removing an activation lock means (not shown), arranged on said housing adjacent the manually operable delivery controller 30 and movable between a tamper proof position in which said manually operable delivery controller is locked for activating the device and a position in which said manually operable delivery controller is released for activating the device. The activation lock means may be arranged with a groove (not shown) in which the scroll wheel segment fits when moved from the locking position to the activation position. In order to activate the device, the user then turns or scrolls the manually operable delivery controller 30 in the direction of the arrow 42, FIG. 1, whereby the release mechanism, the ledge 36, moves out of contact with the front end of the plunger rod 28, FIG. 4. The plunger rod is now free to move forward due to the stored energy of the spring 26, whereby the stopper 25 begins to move forward for delivering the medicament with a determined speed through the delivery member e.g. the needle.

Should the patient or user during the medicament delivery feel that he/she needs to temporarily stop the medicament delivery due to e.g. pain because of the injected medicament, and/or wishes to slow down the medicament delivery speed, the manually operable delivery controller 30 is moved/scrolled further in the direction of the arrow 42. This causes the control speed mechanism, the contact surface 38, to come into contact with the side surface of the plunger rod 28. Due to the shape of the contact surface 38, the further the manually operable delivery controller 30 is moved/scrolled in the direction of the arrow 42, the slower the movement of the plunger rod, until it comes to a stop. The radiuses between the axis and the contact surface 38 and the manually operating surface 35 respectively, are chosen such that it does not require a lot of force to control and stop the movement of the plunger rod 28. In that aspect, the contact surface 38 and/or the side surface of the plunger rod 28, may be provided with friction enhancing means, such as small protrusions, grooves, as well as materials with certain friction enhancing properties.

The wording medicament container may embrace several different types of containers such as cartridges, ampoules, syringes, vials, aerosol containers, just to mention a few. In that respect the present invention could also be used with other types of delivery devices such as powder or aerosol inhalers as well as nebulizers, with a delivery member as a nozzle e.g. a mouth piece or nasal piece and capable of delivering a medicament to be inhaled by the patient.

It is further to be understood that other types of power sources can be used for the delivery of the medicament to a patient, such as leaf springs, clock springs, constant force springs, volute springs, pneumatic or hydraulic springs or any other type of non-electric power source suitable for the intended use according to the present invention.

It is to be understood that the embodiment described above and shown in the drawings is to be regarded only as a non-limiting example of the present invention and that it may be amended in many ways within the scope of the patent claims.

The invention claimed is:

1. A medicament delivery device, comprising:
    a generally elongated tubular housing having a front part and a rear part;
    a medicament container disposed within the front part, wherein the container has a front opening for a delivery member for delivering medicament therethrough;
    a medicament delivery drive unit, comprising a power source and a plunger rod, and arranged to be moved between a cocked position and a released position within the medicament container with a determined speed; and
    a manually operable delivery controller arranged to be rotated between a locked position, in which a release mechanism of the manually operable delivery controller holds the medicament delivery drive unit in the cocked position, and a releasing position, in which the release mechanism releases the medicament delivery drive unit;
    wherein the manually operable delivery controller is further arranged to rotate between the releasing position and a controlling position, in which a control speed mechanism of the manually operable delivery controller interacts with the medicament delivery drive unit for controlling the speed of the medicament delivery drive unit and thereby the medicament delivery speed; the manually operable delivery controller comprises a scroll wheel segment protruding through an opening on a side of the rear part; the scroll wheel segment is turnable around an axis; the release mechanism includes a ledge of the scroll wheel segment interacting with a front end of the plunger rod, such that when the front end of the plunger rod rests onto the ledge, the medicament delivery drive unit is held in the cocked position, and when the scroll wheel segment is moved from the locked position to the releasing position, the ledge is disengaged from the front end of the plunger rod and the medicament delivery drive unit is moved from the cocked position to the released position.

2. The delivery device of claim 1, wherein the control speed mechanism includes a contact surface of the scroll wheel segment interacting with a side surface of the plunger rod, such that when the scroll wheel segment is moved from the releasing position to the control position, the contact surface makes contact with the side surface of the plunger rod for controlling the speed of the medicament delivery drive unit and thereby the medicament delivery speed.

3. The delivery device of claim 2, wherein the contact surface is arranged with friction enhancing members.

4. The delivery device of claim 3, wherein the friction enhancing members include at least one of protrusions, grooves, and ribs.

5. The delivery device of claim 1, wherein the scroll wheel segment comprises a manually operating surface arranged with friction enhancing members.

6. The delivery device of claim 1, wherein the delivery member is a needle or a nozzle.

* * * * *